United States Patent
Kang et al.

(10) Patent No.: US 11,875,878 B2
(45) Date of Patent: Jan. 16, 2024

(54) MACHINE LEARNING METHOD AND APPARATUS USING STEPS FEATURE SELECTION BASED ON GENETIC ALGORITHM

(71) Applicants: IMEDISYNC. LTD., Seoul (KR); THE CATHOLIC UNIVERSITY OF KOREA INDUSTRY-ACADEMIC COOPERATION FOUNDATION, Seoul (KR)

(72) Inventors: Seung Wan Kang, Seoul (KR); Namheon Kim, Paju-si (KR); Dong Won Yang, Seoul (KR)

(73) Assignees: IMEDISYNC. LTD., Seoul (KR); THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 17/624,500

(22) PCT Filed: Nov. 8, 2021

(86) PCT No.: PCT/KR2021/016145
§ 371 (c)(1),
(2) Date: Jan. 3, 2022

(87) PCT Pub. No.: WO2022/139168
PCT Pub. Date: Jun. 30, 2022

(65) Prior Publication Data
US 2022/0399081 A1 Dec. 15, 2022

(30) Foreign Application Priority Data
Dec. 21, 2020 (KR) .......... 10-2020-0180089

(51) Int. Cl.
*G01N 33/48* (2006.01)
*G01N 33/50* (2006.01)
*G16B 40/00* (2019.01)
*G16B 5/00* (2019.01)
*G06N 3/126* (2023.01)

(52) U.S. Cl.
CPC .......... *G16B 40/00* (2019.02); *G06N 3/126* (2013.01); *G16B 5/00* (2019.02)

(58) Field of Classification Search
CPC .......... G16B 40/00; G16B 5/00; G16B 40/20; G16B 50/00; G06N 3/126; G16H 50/20
See application file for complete search history.

(56) References Cited

FOREIGN PATENT DOCUMENTS
KR 10-2008-0082665 9/2008

OTHER PUBLICATIONS

Cornilescu et al. Protein backbone angle restraints from searching a database for chemical shift and sequence homology. Journal of Biomolecular NMR, vol. 13, pp. 289-302. (Year: 1999).*
Mitchell M. Genetic Algorithms: An Overview. Complexity, vol. 1, pp. 31-39, 17 pages. (Year: 1995).*
Al-Qazzaz et al., "Role of EEG as Biomarker in the Early Detection and Classification of Dementia," The Science World Journal, Jun. 30, 2014, 16 pages.
Mohammed et al., "Hybrid Efficient Genetic Algorithm for Big Data Feature Selection Problems," Foundations of Science, Mar. 1, 2019, 17 pages.
Office Action in Korean Appln. No. 10-2020-0180089, dated Mar. 2, 2021, 4 pages (with English translation).
Office Action in Korean Appln. No. 10-2020-0180089, dated Mar. 24, 2021, 2 pages (with English translation).

* cited by examiner

*Primary Examiner* — Russell S Negin
(74) *Attorney, Agent, or Firm* — Fish & Richardson P.C.

(57) ABSTRACT

The present disclosure relates to a machine learning method and apparatus using steps feature selection based on a genetic algorithm, and the machine learning method includes defining a feature set including a plurality of features, generating a plurality of feature combinations including n-dimensional features (n is a natural number) for the feature set, independently constructing feature models for the plurality of feature combinations and calculating prediction accuracy for each of the feature models as a prediction result for a predetermined data set, arranging the feature models according to the prediction accuracy to determine at least one good feature model that satisfies a preset criterion, determining at least one good feature from among features included in a corresponding feature set of the at least one good feature model, and updating the feature set to include only the at least one good feature and re-determining a good feature model for a (n+1)-dimensional feature combination based on the updated feature set.

15 Claims, 6 Drawing Sheets

| sub1 | delta | theta | alpha1 | alpha2 | beta1 | beta2 | beta3 | gamma |
|---|---|---|---|---|---|---|---|---|
| Fp1 | 27.476 | 28.281 | 36.507 | 37.437 | 31.425 | 28.409 | 25.672 | 18.748 |
| Fp2 | 26.694 | 27.565 | 35.921 | 37.0321 | 30.697 | 28.362 | 25.241 | 19.042 |
| F7 | 27.642 | 28.460 | 35.331 | 35.875 | 31.322 | 29.104 | 25.797 | 19.811 |
| F8 | 26.098 | 27.122 | 33.472 | 34.726 | 31.013 | 28.883 | 24.874 | 18.738 |
| F3 | 33.966 | 33.778 | 37.265 | 36.893 | 32.982 | 31.905 | 29.555 | 22.519 |
| F4 | 27.942 | 29.234 | 34.511 | 34.737 | 30.402 | 29.979 | 27.218 | 19.544 |
| Fz | 34.108 | 34.241 | 37.460 | 37.120 | 32.540 | 32.378 | 30.187 | 22.667 |
| T3 | 30.045 | 30.318 | 34.713 | 35.415 | 33.719 | 33.979 | 29.835 | 26.909 |
| T4 | 29.562 | 30.603 | 34.481 | 35.138 | 33.624 | 32.278 | 28.617 | 22.716 |
| C3 | 29.490 | 31.626 | 37.275 | 36.936 | 32.716 | 32.448 | 30.723 | 22.842 |
| C4 | 28.692 | 31.234 | 37.240 | 37.075 | 33.811 | 33.205 | 30.321 | 22.946 |
| Cz | 28.156 | 30.779 | 37.008 | 35.997 | 31.134 | 31.457 | 28.296 | 20.858 |
| T5 | 30.831 | 33.063 | 39.897 | 38.852 | 35.324 | 34.851 | 30.316 | 23.672 |
| T6 | 32.883 | 33.315 | 39.875 | 39.347 | 34.616 | 34.039 | 29.350 | 21.961 |
| P3 | 28.715 | 31.163 | 39.358 | 41.309 | 37.149 | 33.923 | 30.834 | 21.955 |
| P4 | 29.377 | 31.839 | 41.130 | 41.661 | 34.951 | 32.977 | 29.846 | 21.584 |
| Pz | 31.447 | 33.139 | 39.713 | 40.656 | 34.882 | 32.486 | 29.980 | 21.737 |
| O1 | 30.810 | 34.452 | 42.412 | 41.772 | 37.836 | 35.501 | 30.961 | 22.879 |
| O2 | 30.401 | 33.899 | 41.777 | 41.017 | 35.469 | 34.666 | 30.307 | 22.408 |

710 brackets the left side of the table.

| Feature | Count | Feature | Count |
|---|---|---|---|
| F4b2 | 359 | Fp2b3 | 123 |
| F4b3 | 346 | F4b3 | 96 |
| Czb3 | 290 | Czb3 | 85 |
| F4d | 272 | C3b3 | 52 |
| O2a2 | 271 | Fp1d | 44 |
| Pzd | 243 | F4b2 | 38 |
| Czb2 | 240 | Pzd | 31 |
| O1b2 | 237 | Czb2 | 27 |
| Fzb2 | 231 | F4d | 27 |
| O1a2 | 215 | O1d | 23 |
| C4d | 203 | C4d | 22 |
| T3a2 | 200 | Fp2b2 | 20 |
| C3b3 | 191 | O1b2 | 20 |
| T5b2 | 186 | O1a2 | 19 |
| Pzb1 | 176 | T3a2 | 18 |
| F3b2 | 171 | Fp1b2 | 18 |
| F4b1 | 162 | O2a2 | 16 |
| C3b2 | 162 | Fzb2 | 16 |

830 brackets the upper portion of the left column.

Fig. 9

| | m1 | m2 | m3 | m4 | m5 | m6 | m7 | m8 | m9 | m10 | m11 | m12 | | score | pred | real |
|---|---|---|---|---|---|---|---|---|---|---|---|---|---|---|---|---|
| ↑ 22 MCI | 21 | 21 | 22 | 22 | 22 | 22 | 21 | 22 | 21 | 21 | 21 | 22 | | 21.57377 | 22 | 21 |
| | 22 | 21 | 22 | 21 | 21 | 21 | 21 | 22 | 22 | 22 | 22 | 22 | | 21.53571 | 22 | 21 |
| | 21 | 21 | 22 | 22 | 21 | 21 | 21 | 21 | 22 | 22 | 21 | 21 | | 21.5082 | 22 | 21 |
| | 21 | 22 | 22 | 21 | 22 | 21 | 21 | 21 | 22 | 21 | 22 | | | 21.39344 | 21 | 21 |
| | 21 | 21 | 21 | 22 | 22 | 21 | 21 | 22 | 21 | 21 | 21 | | | 21.36066 | 21 | 21 |
| | 21 | 21 | 22 | 21 | 21 | 21 | 22 | 22 | 21 | 21 | 22 | | | 21.32787 | 21 | 21 |
| | 22 | 21 | 22 | 21 | 22 | 21 | 22 | 21 | 21 | 21 | 22 | | | 21.29508 | 21 | 21 |
| | 21 | 21 | 21 | 21 | 22 | 21 | 21 | 21 | 21 | 21 | 21 | | | 21.2459 | 21 | 21 |
| | 21 | 21 | 21 | 21 | 22 | 21 | 21 | 22 | 21 | 21 | 21 | | | 21.22951 | 21 | 21 |
| | 21 | 21 | 21 | 22 | 21 | 22 | 21 | 22 | 21 | 21 | 21 | | | 21.21311 | 21 | 21 |
| | 22 | 21 | 21 | 21 | 21 | 21 | 21 | 21 | 21 | 21 | 22 | | | 21.14754 | 21 | 21 |
| | 21 | 22 | 21 | 22 | 21 | 21 | 21 | 21 | 22 | 21 | 21 | 21 | | 21.14754 | 21 | 21 |
| | 21 | 21 | 21 | 22 | 22 | 21 | 21 | 21 | 21 | 21 | 21 | | | 21.13115 | 21 | 21 |
| | 21 | 21 | 21 | 21 | 21 | 21 | 22 | 21 | 21 | 21 | 21 | | | 21.13115 | 21 | 21 |
| | 21 | 21 | 21 | 21 | 21 | 21 | 22 | 21 | 22 | 21 | | | | 21.11475 | 21 | 21 |
| | 21 | 21 | 21 | 21 | 22 | 21 | 21 | 21 | 21 | 21 | 21 | | | 21.09836 | 21 | 21 |
| ↓ Normal 21 | 21 | 21 | 22 | 21 | 21 | 21 | 21 | 21 | 21 | 21 | 21 | | | 21.09836 | 21 | 21 |
| | 21 | 21 | 21 | 21 | 21 | 22 | 21 | 21 | 21 | 21 | 21 | | | 21.08197 | 21 | 21 |

| | score | pred | real |
|---|---|---|---|
| ↑ 22 MCI | 21.57377 | 22 | 21 |
| | 21.53571 | 22 | 21 |
| | 21.5082 | 22 | 21 |
| | 21.39344 | 21 | 21 |
| | 21.36066 | 21 | 21 |
| | 21.32787 | 21 | 21 |
| | 21.29508 | 21 | 21 |
| | 21.2459 | 21 | 21 |
| | 21.22951 | 21 | 21 |
| | 21.21311 | 21 | 21 |
| | 21.14754 | 21 | 21 |
| | 21.14754 | 21 | 21 |
| | 21.13115 | 21 | 21 |
| | 21.13115 | 21 | 21 |
| | 21.11475 | 21 | 21 |
| | 21.09836 | 21 | 21 |
| ↓ Normal 21 | 21.09836 | 21 | 21 |
| | 21.08197 | 21 | 21 |

1010

(b)

| score | pred |
|---|---|
| 21.5082 | 22 |
| 21.44263 | 21 |
| 21.42623 | 21 |
| 21.36066 | 21 |
| 21.34427 | 21 |
| 21.31148 | 21 |
| 21.27869 | 21 |
| 21.2623 | 21 |
| 21.2459 | 21 |
| 21.22951 | 21 |
| 21.21311 | 21 |
| 21.19672 | 21 |
| 21.18033 | 21 |
| 21.21311 | 21 |
| 21.14754 | 21 |
| 21.13115 | 21 |
| 21.14754 | 21 |
| 21.16393 | 21 |

(c)

| score | pred |
|---|---|
| 21.42623 | 22 |
| 21.40984 | 22 |
| 21.39344 | 22 |
| 21.34427 | 21 |
| 21.34427 | 21 |
| 21.31148 | 21 |
| 21.31148 | 21 |
| 21.2459 | 21 |
| 21.2623 | 21 |
| 21.21311 | 21 |
| 21.21311 | 21 |
| 21.19672 | 21 |
| 21.18033 | 21 |
| 21.21311 | 21 |
| 21.19672 | 21 |
| 21.18033 | 21 |
| 21.18033 | 21 |
| 21.19672 | 21 |

MACHINE LEARNING METHOD AND APPARATUS USING STEPS FEATURE SELECTION BASED ON GENETIC ALGORITHM

CROSS-REFERENCE TO RELATED APPLICATIONS

This application is a National Stage Application under 35 U.S.C. § 371 and claims the benefit of International Application No. PCT/KR2021/016145, filed on Nov. 8, 2021, which claims the benefit of priority to Korean Application No. 10-2020-0180089 filed Dec. 21, 2020, the entire contents of each of which is incorporated herein by reference in the disclosure of this application.

FIELD OF THE DISCLOSURE

The present disclosure relates to a technique for steps selection of variables for machine learning, and more particularly, to a machine learning method and apparatus using steps feature selection based on a genetic algorithm capable of rationally reducing a search space using the genetic algorithm and extracting features having the best approximate performance for determining a change in electroencephalogram (EEG) according to a disease.

RELATED ART

The number of patients with dementia, a geriatric disease, is also increasing rapidly with the aging population in major advanced countries at home and abroad. In addition, medical service costs due to dementia are also increasing exponentially, and thus, the importance of early detection and prevention of dementia is being emphasized. On the other hand, it is known that a protein called beta amyloid is found at a high rate in brains of dementia patients.

The medical community judges that if beta amyloid is found in a brain of a patient with mild cognitive impairment (MCI), which is a previous stage of dementia, the patient is highly likely to develop into dementia. Therefore, in order to receive a prescription for a drug to alleviate a progression of dementia, it is necessary to check the beta amyloid in the brain. As a conventional method of determining the presence or absence of beta amyloid in a brain, there is an amyloid PET test. However, the amyloid PET test is generally an expensive technique, and does not guarantee that people with dementia will get a positive result and get a prescription for medication.

Meanwhile, electroencephalogram (EEG) is a method that is relatively low-cost and physically less burdensome among various methods of measuring brain activity. Recently, with the development of machine learning and deep learning technology, the method of diagnosing pathological symptoms by measuring electroencephalogram has become more advanced. In this case, which channel and frequency of the EEG reveal features different from those of normal people, and the patterns differ depending on the disease. For successful prediction of disease, it is necessary to identify an optimal channel and frequency in which the change is noticeably revealed.

PRIOR ART DOCUMENT

Patent Literature

Korean Patent Laid-Open Publication No. 10-2008-0082665 (Sep. 11, 2008)

DETAILED DESCRIPTION OF THE INVENTION

Technical Problem

In view of the above, the present disclosure provides a machine learning method and apparatus using steps feature selection based on a genetic algorithm capable of rationally reducing a search space using the genetic algorithm and extracting features having the best approximate performance for determining a change in electroencephalogram (EEG) according to a disease.

The present disclosure provides a machine learning method and apparatus using steps feature selection based on a genetic algorithm capable of performing a test and diagnosis at low cost by constructing a high-accuracy learning model that classifies various pathological symptoms based on spatial/frequency features of electroencephalogram.

Technical Solution

A machine learning method and apparatus using steps feature selection based on a genetic algorithm includes defining a feature set including a plurality of features, generating a plurality of feature combinations including n-dimensional features (n is a natural number) for the feature set, independently constructing feature models for the plurality of feature combinations and calculating prediction accuracy for each of the feature models as a prediction result for a predetermined data set, arranging the feature models according to the prediction accuracy to determine at least one good feature model that satisfies a preset criterion, determining at least one good feature from among features included in a corresponding feature set of the at least one good feature model, and updating the feature set to include only the at least one good feature and re-determining a good feature model for a (n+1)-dimensional feature combination based on the updated feature set.

The defining of the feature set may include defining, as the plurality of features, combinations between an electroencephalogram occurrence location and an electroencephalogram frequency band for an electroencephalogram signal.

The defining of the feature set may include determining a scalp electrode location depending on a 10-20 system as the electroencephalogram occurrence location, and separately determining the electroencephalogram frequency band into delta, theta, alpha, beta, and gamma according to a frequency component of the electroencephalogram signal.

The generating of the plurality of feature combinations may include generating the plurality of feature combinations corresponding to all combinations including n features among the plurality of features.

The calculating of each of the prediction accuracy may include calculating the prediction accuracy based on whether each of the feature models matches a predicted value and an actual value regarding the presence or absence of amyloid for the predetermined data set.

The determining of the good feature model may include determining top m (m is a natural number) feature models as the at least one good feature model according to the order of high prediction accuracy.

The determining of the good feature may include counting the number of frequencies of each feature of the corresponding feature set and determining top k (k is a natural number) features as the at least one good feature according to the order of high frequency.

The re-determining of the good feature model may include repeatedly performing a re-determining process on the good feature model according to an update of the feature set and an increase in a dimension of the feature combination, and ending of the repetition of the re-determining process in a case where a difference between the prediction accuracy for the corresponding good feature model and the prediction accuracy for the previous step is less than or equal to a preset reference value.

The re-determining of the good feature model may include comparing an average or minimum value of the corresponding prediction accuracy with the prediction accuracy for the previous step in a case where the number of corresponding good feature models is plural.

The machine learning method may further include performing reinforcement learning on the good feature model according to the result of predicting the good feature model for the predetermined data set.

The performing of the reinforcement learning may include adjusting the corresponding predicted value by applying a reinforcement factor to the corresponding predicted value when the predicted result matches the actual value.

The reinforcement factor may be calculated by applying a specific multiple based on an average value of the predicted result when the number of good feature models is plural.

The reinforcement factor may be calculated through the following equation based on the average value and the specific multiple.

$$\alpha = 1 + \beta * x \quad \text{[Equation]}$$

(Where $\alpha$ denotes a reinforcement factor, $\beta$ denotes a value less than or equal to a decimal point of the average value, and x denotes a specific multiple.)

A machine learning apparatus using steps feature selection based on a genetic algorithm includes a feature set definition unit configured to define a feature set including a plurality of features, a feature combination generation unit configured to generate a plurality of feature combinations including n-dimensional features (n is a natural number) for the feature set, a feature model analysis unit configured to independently construct feature models for the plurality of feature combinations and calculate prediction accuracy for each of the feature models as a prediction result for a predetermined data set, a good feature model determination unit configured to align the feature models according to the prediction accuracy to determine at least one good feature model that satisfies a preset criterion, a good feature extraction unit configured to determine at least one good feature from among the features included in a corresponding feature set of the at least one good feature model, and a model performance improvement unit configured to update the feature set to include only the at least one good feature and re-determine a good feature model for a (n+1)-dimensional feature combination based on the updated feature set.

Advantageous Effects

The disclosed technology may have the following effects. However, since a specific embodiment is not construed as including all of the following effects or only the following effects, it should not be understood that the scope of the disclosed technology is limited to the specific embodiment.

According to an embodiment of the present disclosure, a machine learning method and apparatus using steps feature selection based on a genetic algorithm can rationally reduce a search space using the genetic algorithm and extract features having the best approximate performance for determining a change in electroencephalogram (EEG) according to a disease.

According to an embodiment of the present disclosure, a machine learning method and apparatus using steps feature selection based on a genetic algorithm can perform a test and diagnosis at low cost by constructing a high-accuracy learning model that classifies various pathological symptoms based on spatial/frequency features of electroencephalogram.

BRIEF DESCRIPTION OF THE DRAWINGS

FIG. 7 is a diagram for describing an embodiment of a feature set according to the present disclosure.

FIG. 8 is a diagram for describing a process of calculating the number of frequencies of features found in a good feature model according to the present disclosure.

FIGS. 9 to 11 are diagrams for describing a reinforcement learning process for the good feature model according to the present disclosure.

FIG. 12 is a diagram for describing a graph regarding performance of a machine learning model according to the present disclosure.

DESCRIPTION OF EXEMPLARY EMBODIMENTS

Figure 1:
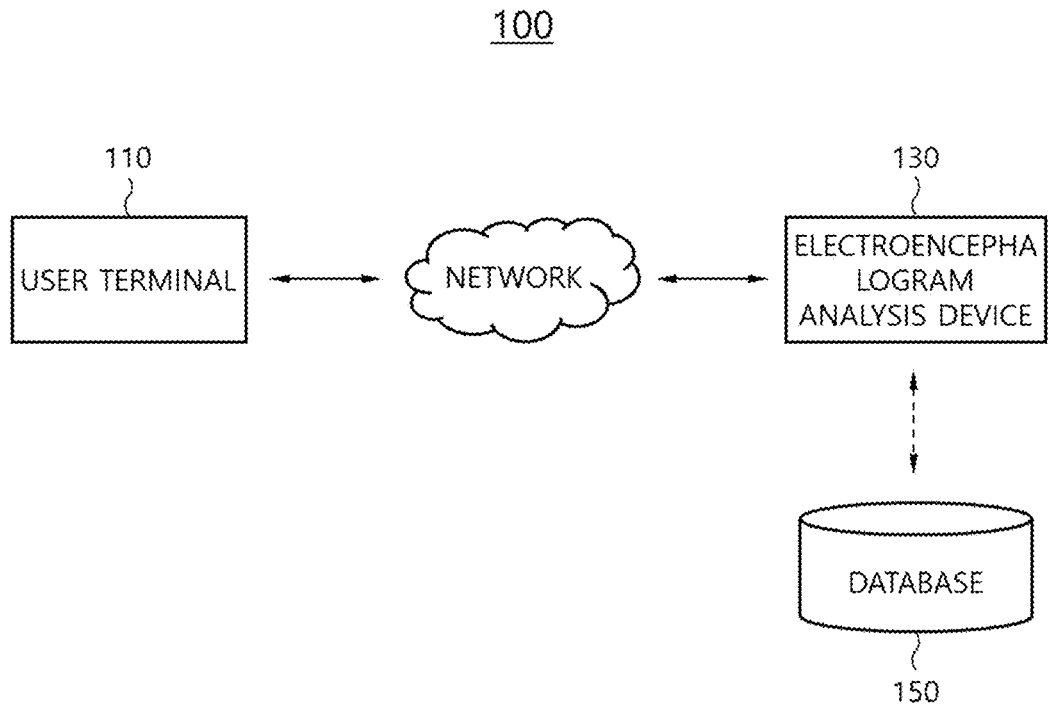
FIG. 1 is a diagram for describing an electroencephalogram analysis system according to the present disclosure.

Since the description of the present disclosure is merely an embodiment for structural or functional explanation, the scope of the present disclosure should not be construed as being limited by the embodiments described in the text. That is, since the embodiments may be variously modified and may have various forms, the scope of the present disclosure should be construed as including equivalents capable of realizing the technical idea. In addition, a specific embodiment is not construed as including all the objects or effects presented in the present disclosure or only the effects, and therefore the scope of the present disclosure should not be understood as being limited thereto.

On the other hand, the meaning of the terms described in the present application should be understood as follows.

Terms such as "first" and "second" are intended to distinguish one component from another component, and the scope of the present disclosure should not be limited by these terms. For example, a first component may be named a second component and the second component may also be similarly named the first component.

It is to be understood that when one element is referred to as being "connected to" another element, it may be connected directly to or coupled directly to another element or be connected to another element, having the other element intervening therebetween. On the other hand, it is to be understood that when one element is referred to as being "connected directly to" another element, it may be connected to or coupled to another element without the other element intervening therebetween. Meanwhile, other expressions describing a relationship between components, that is, "between", "directly between", "neighboring to", "directly neighboring to" and the like, should be similarly interpreted.

It should be understood that the singular expression includes the plural expression unless the context clearly indicates otherwise, and it will be further understood that the terms "comprises" or "have" used in this specification, specify the presence of stated features, steps, operations, components, parts, or a combination thereof, but do not preclude the presence or addition of one or more other features, numerals, steps, operations, components, parts, or a combination thereof.

In each step, an identification code (for example, a, b, c, and the like) is used for convenience of description, and the identification code does not describe the order of each step, and each step may be different from the specified order unless the context clearly indicates a particular order. That is, the respective steps may be performed in the same sequence as the described sequence, be performed at substantially the same time, or be performed in an opposite sequence to the described sequence.

The present disclosure can be embodied as computer readable code on a computer-readable recording medium, and the computer-readable recording medium includes all types of recording devices in which data can be read by a computer system. An example of the computer readable recording medium may include a read only memory (ROM), a random access memory (RAM), a compact disk read only memory (CD-ROM), a magnetic tape, a floppy disk, an optical data storage, or the like. In addition, the computer readable recording medium may be distributed in computer systems connected to each other through a network, such that the computer readable codes may be stored in a distributed scheme and executed.

Unless defined otherwise, all the terms used herein including technical and scientific terms have the same meaning as meanings generally understood by those skilled in the art to which the present disclosure pertains. It should be understood that the terms defined by the dictionary are identical with the meanings within the context of the related art, and they should not be ideally or excessively formally defined unless the context clearly dictates otherwise.

FIG. 1 is a diagram for describing an electroencephalogram analysis system according to the present disclosure.

Referring to FIG. 1, an electroencephalogram analysis system 100 may include a user terminal 110, an electroencephalogram analysis device 130, and a database 150.

The user terminal 110 may correspond to a computing device capable of generating data for electroencephalogram analysis and confirming an electroencephalogram analysis result. That is, the user terminal 110 may correspond to a measurement device that is attached to the user to measure a user's electroencephalogram signal and collect the signal. In addition, the user terminal 110 may be implemented as a smartphone, a notebook, or a computer that is operated by being connected to the electroencephalogram analysis device 130, but is not necessarily limited thereto, and may be implemented in various devices such as a tablet PC. In this case, the user terminal 110 may be implemented to collect an electroencephalogram signal in conjunction with a separate signal measurement device and transmit the corresponding information to the electroencephalogram analysis.

That is, the user terminal 110 may be connected to the electroencephalogram analysis device 130 through a network, and the plurality of user terminals 110 may be simultaneously connected to the electroencephalogram analysis device 130. In addition, the user terminal 110 may access the electroencephalogram analysis system 100 to install and execute a dedicated program or application that may use a predetermined service.

The electroencephalogram analysis device 130 may be implemented as a server corresponding to a computer or program that may train electroencephalogram signals and pathological symptom diagnosis data of various users, and analyze the electroencephalogram signal based on this to generate various types of analysis information. The electroencephalogram analysis device 130 may be connected to the user terminal 110 through a wired network or a wireless network such as Bluetooth or WiFi, and may transmit/receive data to and from the user terminal 110 through the network. In addition, the electroencephalogram analysis device 130 may be implemented to operate in conjunction with a separate external system (not illustrated in FIG. 1) in order to collect data or provide an additional function.

In an embodiment, the electroencephalogram analysis device 130 may be implemented including the machine learning apparatus according to the present disclosure. That is, the electroencephalogram analysis device 130 may diagnose and predict various pathological symptoms by analyzing the user's electroencephalogram signal using a learning model constructed by the machine learning apparatus according to the present disclosure. In addition, the electroencephalogram analysis device 130 may construct an independent learning model using the machine learning method according to the present disclosure, and may perform the electroencephalogram analysis using the learning model. Accordingly, the electroencephalogram analysis device 130 of the electroencephalogram analysis system 100 may be understood as a configuration corresponding to the machine learning apparatus according to the present disclosure, if necessary.

The database 150 may correspond to a storage device for storing various types of information required in an operation process of the electroencephalogram analysis device 130. For example, the database 150 may store learning data for machine learning collected from various sources, and may store information about the learning model constructed through the machine learning, but is not limited thereto, and the electroencephalogram analysis device 130 may store information collected or processed in various forms in a machine learning process using steps feature selection based on a genetic algorithm.

Meanwhile, in FIG. 1, the database 150 is illustrated as a device independent of the electroencephalogram analysis device 130, but is not necessarily limited thereto, and may be implemented by being included in the electroencephalogram analysis device 130 as a logical storage device of the electroencephalogram analysis device 130.

Figure 2:
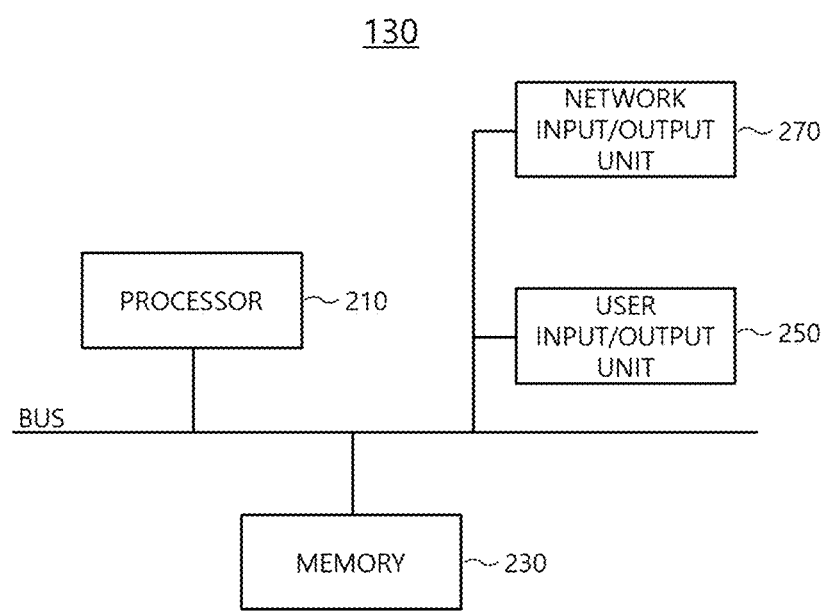
FIG. 2 is a diagram for describing a system configuration of the electroencephalogram analysis device of FIG. 1.

FIG. 2 is a diagram for describing a system configuration of the electroencephalogram analysis apparatus of FIG. 1.

Referring to FIG. 2, the electroencephalogram analysis device 130 may be implemented including a processor 210, a memory 230, a user input/output unit 250, and a network input/output unit 270.

The processor 210 may execute a procedure for processing each step in the process of operating the electroencephalogram analysis device 130, manage the memory 230 to be read or written throughout the process, and schedule a synchronization time between a volatile memory and a non-volatile memory in the memory 230. The processor 210 may control the overall operation of the electroencephalogram analysis device 130, and may be electrically connected to the memory 230, the user input/output unit 250, and the network input/output unit 270 to control the flow of data therebetween. The processor 210 may be implemented as a central processing unit (CPU) of the electroencephalogram analysis device 130.

The memory 230 is implemented as a non-volatile memory, such as a solid state drive (SSD) or a hard disk drive (HDD), and may include an auxiliary storage device used to store overall data necessary for the electroencephalogram analysis device 130 and may include a main storage device implemented as a volatile memory such as random access memory (RAM).

The user input/output unit 250 may include an environment for receiving user input and an environment for outputting specific information to a user. For example, the user input/output unit 250 may include an input device including an adapter such as a touch pad, a touch screen, an on-screen keyboard, or a pointing device, and an output device including an adapter such as a monitor or a touch screen. In an embodiment, the user input/output unit 250 may correspond to a computing device connected via remote access. In this case, the electroencephalogram analysis device 130 may be performed as an independent server.

The network input/output unit 270 includes an environment for connecting with an external device or a system through a network, and may include an adapter for communication, for example, a local area network (LAN), a metropolitan area network (MAN), a wide area network (WAN), a value added network (VAN), and the like.

Figure 3:
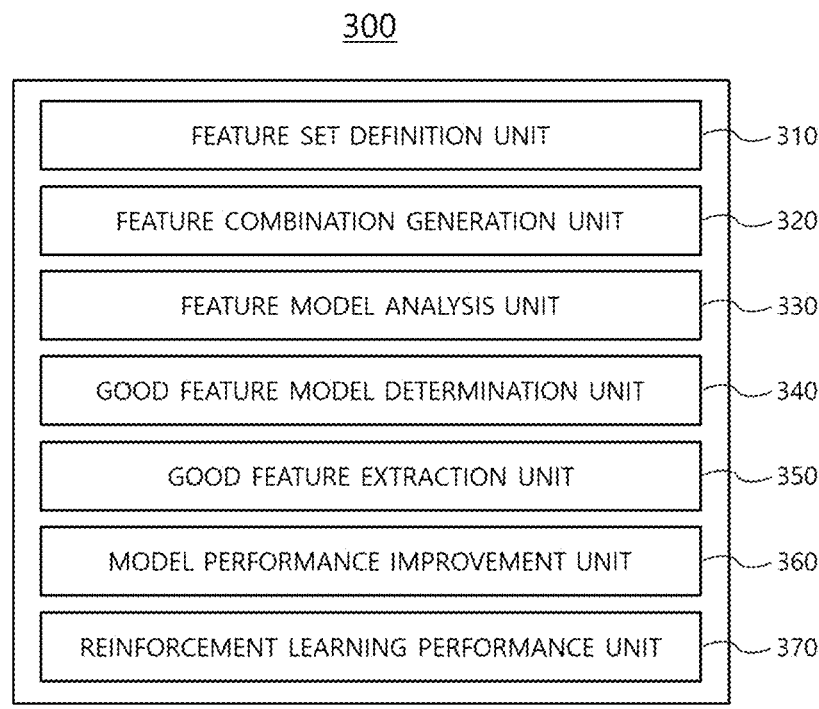
FIG. 3 is a diagram for describing a functional configuration of a machine learning apparatus according to the present disclosure.

FIG. 3 is a diagram for describing a functional configuration of a machine learning apparatus according to the present disclosure.

Referring to FIG. 3, the machine learning apparatus 300 may include a feature set definition unit 310, a feature combination generation unit 320, a feature model analysis unit 330, a good feature model determination unit 340, and a good feature extraction unit 350, a model performance improvement unit 360, a reinforcement learning performance unit 370, and a control unit (not illustrated in FIG. 3).

The feature set definition unit 310 may define a feature set including a plurality of features. Here, the feature set may correspond to a set including features, and the feature may correspond to information about characteristics specifying data. The feature set defined by the feature set definition unit 310 may serve to specify a range of learning data in the machine learning process using steps feature selection based on a genetic algorithm.

In an embodiment, the feature set definition unit 310 may define, as a plurality of features, combinations between an electroencephalogram occurrence location and an electroencephalogram frequency band for an electroencephalogram signal. More specifically, the user's electroencephalogram signal may correspond to an electrical signal obtained by non-invasively measuring electrical activity by an electrode attached to a head surface of a brain, and may be measured by various signal values depending on the electroencephalogram occurrence location and the electroencephalogram frequency band. Here, the electroencephalogram occurrence location may correspond to a location where electroencephalogram occurs, and may correspond to a location of an electrode, to which an electroencephalogram measuring device is attached, to measure electroencephalogram. Also, the electroencephalogram frequency band may correspond to a frequency range set to decompose the electroencephalogram signal into various frequency components. That is, the feature set definition unit 310 may define various combinations between the electroencephalogram occurrence location and the electroencephalogram frequency band as features, and each feature may be configured as information specifying the electroencephalogram occurrence location and the electroencephalogram frequency band.

In an embodiment, the feature set definition unit 310 may determine a scalp electrode location depending on a 10-20 system as the electroencephalogram occurrence location and separately determine the electroencephalogram frequency band into delta, theta, alpha, beta, and gamma according to the frequency component of the electroencephalogram signal The 10-20 system may correspond to a representative method of defining the location of the scalp electrode for measuring the electroencephalogram. "10" and "20" may correspond to the fact that the actual distance between adjacent electrodes is 10% or 20% of a total anterior-posterior or right-side distance of a skull. The locations of each electrode may be represented by a frontal lobe (Fp), a frontal lobe (F), a temporal sphere (T), a parietal (P), an occipital (O), and a central (C).

In addition, the electroencephalogram frequency band may be defined as delta 0 to 4 Hz, theta 4 to 8 Hz, alpha 8 to 13 Hz, beta 13 to 30 Hz, and gamma 30 to 50 Hz. For example, the feature set definition unit 310 may define a specific feature as "Fp1d", and in this case, the corresponding feature may correspond to a signal value of a delta wave measured at the location of the Fp1 electrode.

The feature combination generation unit may generate a plurality of feature combinations including n-dimensional features (n is a natural number) for the feature set. The feature combination generation unit 320 may generate feature combinations for each dimension by using various features defined as a feature set. In this case, the dimension may correspond to the number of features constituting the feature combination. For example, a one-dimensional feature combination may include one feature, and a two-dimensional feature combination may include two features. The machine learning apparatus 300 may specify in advance a start dimension of a feature combination for steps feature selection, and the feature combination generation unit 320 may generate a feature combination corresponding to the dimension with reference to the start dimension.

In an embodiment, the feature combination generation unit 320 may generate a plurality of feature combinations in response to all combinations including n features among the plurality of features. The feature combination generation unit 320 may selectively generate a feature combination including the number of features corresponding to the corresponding dimension for a specified dimension, and generate all feature combinations for the corresponding dimension as necessary. For example, when the feature set includes a total of 10 features, 10 one-dimensional feature combinations, 45 two-dimensional feature combinations, 120 three-dimensional feature combinations, etc. may be generated, respectively.

The feature model analysis unit 330 may independently construct feature models for the plurality of feature combinations and calculate prediction accuracy for each of the feature models as a prediction result for a predetermined data set. The feature model analysis unit 330 may generate a feature model by independently training corresponding training data for possible feature combinations within a predetermined dimension. In this case, as the learning algorithm, a support vector machine (SVM), K-means clustering, a decision tree, or the like may be used. The feature model analysis unit 330 may calculate prediction accuracy for each model by using a predetermined test set after each learning model is constructed. The prediction accuracy may be derived as a ratio of the number of successful predictions to the number of test data.

In an embodiment, the feature model analysis unit 330 may calculate prediction accuracy based on whether each of the feature models matches a predicted value and an actual value regarding the presence or absence of amyloid for a predetermined data set. When a feature set related to the electroencephalogram signal is defined and feature models for electroencephalogram analysis are constructed for the combination of features related to the electroencephalogram occurrence location and the electroencephalogram frequency band, the feature model analysis unit 330 may acquire the predicted value regarding the presence or absence of amyloid by inputting each test data of a predetermined data set into the feature model. The feature model analysis unit 330 may calculate prediction accuracy for each model by counting whether the predicted value predicted by the feature model matches the actual value. The feature model may have various prediction probabilities according to the characteristics of the training data used for learning, and the feature model analysis unit 330 may calculate the prediction accuracy for each model and analyze a correlation between the characteristics of the training data used to construct each model and the prediction of the presence or absence of amyloid.

The good feature model determination unit 340 may determine at least one good feature model that satisfies a preset criterion by aligning the feature models according to prediction accuracy. The good feature model determination unit 340 may determine, as a good feature model, a feature model evaluated as having good prediction performance among previously constructed feature models. To this end, the good feature model determination unit 340 may set a criterion for prediction accuracy for the feature model. For example, when the criterion regarding the prediction accuracy is set to 90%, the good feature model determination unit 340 may select feature models having a prediction accuracy for 90% or more for the test set and determine the selected feature models as a good feature model.

Meanwhile, the good feature model determination unit 340 may determine the good feature model according to the adjusted criterion after adjusting the preset criterion by a predetermined ratio when there is no feature model that satisfies the preset criterion. The machine learning method according to the present disclosure may operate in such a way that the performance of the learning model is gradually improved through repetitive feature selection and learning, and thus, even if the initially constructed feature models do not meet the preset criteria, the models may be implemented in a flexible control manner so that the criterion is dynamically adjusted to repeatedly operate the feature selection and learning.

In an embodiment, the good feature model determination unit 340 may determine top m (m is a natural number) feature models as at least one good feature model in the order of high prediction accuracy. That is, the good feature model determination unit 340 may determine the good feature model based on whether the absolute criterion is satisfied, and the top m feature models may be sequentially determined as good feature models on a list aligned according to the relative criterion of prediction accuracy. Through this, a predetermined good feature model is selected in each step without a separate absolute reference setting, so that the operation to the next step may proceed naturally. Meanwhile, m may be set in advance through the machine learning apparatus 300 and may be set to various values according to the operating environment or conditions.

The good feature extraction unit 350 may determine at least one good feature from among features included in a corresponding feature set of at least one good feature model. Features used to construct a good feature model with relatively good performance may be expected to have a closer correlation with the corresponding prediction result than other features, and the good feature extraction unit 350 may determine a good feature from features used to construct a good feature model. That is, the good feature may correspond to a feature having a relatively high correlation with analysis information to be predicted through the feature model, and may be included in the updated feature set in the operation process of the next stage.

In an embodiment, the good feature extraction unit 350 may count the number of frequencies of each feature of the corresponding feature set and determining top k (k is a natural number) features as at least one good feature according to the order of high frequency. That is, the good feature may correspond to a feature used more frequently in the good feature models, and the good feature extraction unit 350 may calculate the number of frequencies for each feature by aggregating the features used in each good feature model. In addition, the good feature extraction unit 350 may determine only the top k features as good features after being aligned according to the aggregated frequency for each feature. In this case, k may be set in advance through the machine learning apparatus 300 and may be set to various values according to the operating environment or conditions. Meanwhile, the good feature extraction unit 350 may apply an absolute reference value to the aggregated number of frequencies for each feature to determine a feature having a frequency greater than the reference value as a good feature.

The model performance improvement unit 360 may update the feature set to include only at least one good feature, and re-determine the good feature model for a (n+1)-dimensional feature combination based on the updated feature set. More specifically, good features determined by the good feature extraction unit 350 in the current stage may be defined as a feature set in the next stage, and the process of determining the event feature model may be repeatedly performed through the generation of the feature combination and the construction and verification of the feature model for the updated feature set.

In this case, the feature combination generated for the updated feature set may be set to be one dimension higher than the dimension of the previous stage. That is, as the dimension of the feature combination increases, the number of cases increases and the amount of computation for processing them may also increase, which may negatively affect the overall operation speed or performance. Therefore, the model performance improvement unit 360 may effectively reduce the amount of computation required in the modeling process by generating a combination of features only with the good features of the previous stage while gradually increasing the dimension for each stage.

In an embodiment, the model performance improvement unit 360 may repeatedly perform the re-determination process for the good feature model according to the update of the feature set and the increase in the dimension of the feature combination, and terminate the repetition of the re-determination process when the difference between the prediction accuracy for the corresponding good feature model and the prediction accuracy for the previous stage is less than or equal to the preset reference value. The model performance improvement unit 360 may gradually increase the dimension of the feature combination as the stage proceeds, and as the dimension increases, the prediction performance of the feature model constructed through the machine learning may also increase. However, after repeating a predetermined stage, the change in the performance of the generated feature model may not be large, and accordingly, the model performance improvement unit 360 may terminate the repetitive operation for improving performance when the change is less than or equal to a preset reference value through the performance comparison between the good feature model of the previous stage and the good feature model of the current stage and determine the good feature model generated in the last stage as the final learning result.

In an embodiment, the model performance improvement unit 360 may compare the average or minimum value of the corresponding prediction accuracy with the prediction accuracy for the previous step when the number of corresponding good feature models is plural. When there is only one good feature model, only the prediction accuracy for the corresponding model may be compared with that of the previous step. When the number of good feature models is plural, it can be compared with that of the previous stage based on any one of the average, minimum, and maximum values of the prediction accuracy for each model. On the other hand, it goes without saying that various methods as well as the above method can be applied to the performance comparison operation of the good feature models of the current stage and the previous stage.

The reinforcement learning performance unit 370 may perform reinforcement learning for the good feature model according to the result predicted by the good feature model for a predetermined data set. The reinforcement learning is one of machine learning, and may correspond to a method that is inspired by behavioral psychology to allow an agent defined in a certain environment to recognize a current state and select a behavior of maximizing compensation among selectable behaviors or a behavior order. The reinforcement learning performance unit 370 may compensate for the relatively low accuracy for the prediction performance by performing reinforcement learning for the good feature model.

In an embodiment, the reinforcement learning performance unit 370 may adjust the predicted value by applying the reinforcement factor to the predicted value when the predicted result matches the actual value. Here, the reinforcement factor may correspond to a coefficient applied as a multiplication operation to the prediction result for the reinforcement learning. That is, the reinforcement learning performance unit 370 may perform the reinforcement learning by applying a predetermined reinforcement factor to the predicted value when the predicted value and the actual value for each even prediction model match. For example, in predicting the presence or absence (or +/−) of amyloid based on the electroencephalogram signal, the reinforcement learning performance unit 370 may independently perform depending on the amyloid "+" or "−" in the case where the predicted value matches the actual value.

In an embodiment, the reinforcement factor may be calculated by applying a specific multiple based on the average value of the predicted result when the number of good feature models is plural. The reinforcement factor may be calculated for each multiple, and any one of a plurality of multiples may be selectively applied by the reinforcement learning performance unit 370. In particular, the reinforcement factor may be specifically calculated using the average value of the prediction results of the good feature models, and the reinforcement learning for each good feature model may be performed based on the calculated average value. As a result, the reinforcement learning performance unit 370 may supplement the prediction performance of each good feature model through the reinforcement learning.

In an embodiment, the reinforcement factor may be calculated through the following equation based on the average value and the specific multiple.

$$\alpha = 1 + \beta * x \qquad \text{[Equation]}$$

Here, $\alpha$ denotes a reinforcement factor, $\beta$ denotes a value less than or equal to a decimal point of the average value, and x denotes a specific multiple. This will be described in more detail with reference to FIGS. 9 to 11.

The control unit (not illustrated in FIG. 3) controls the overall operation of the machine learning apparatus 300, and may manage a control flow or a data flow between the feature set definition unit 310, the feature combination generation unit 320, the feature model analysis unit 330, even the feature model determination unit 340, the good feature extraction unit 350, the model performance improvement unit 360, and the reinforcement learning performance unit 370.

Figure 4:
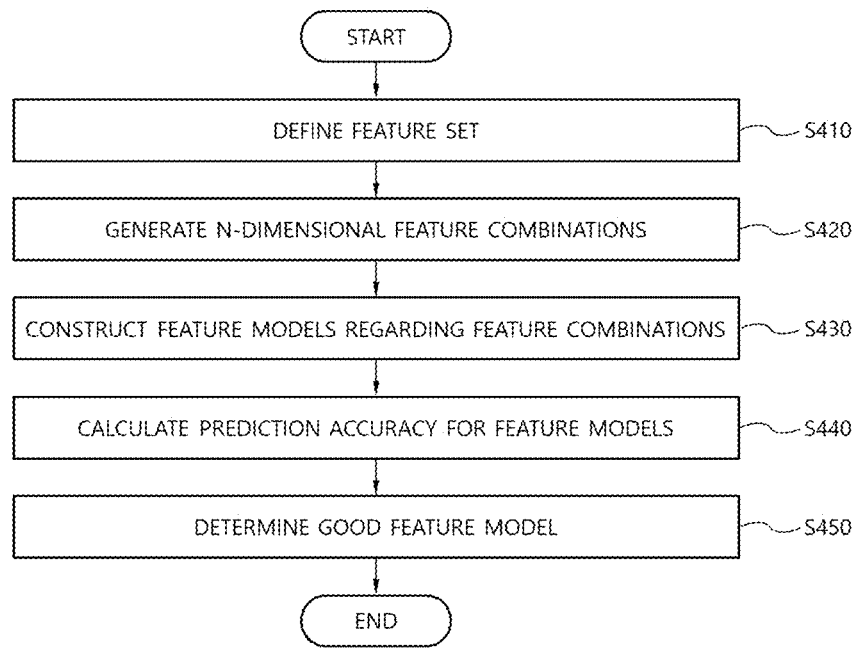
FIG. 4 is a flowchart illustrating a machine learning method according to the present disclosure.

FIG. 4 is a flowchart illustrating a machine learning method according to the present disclosure.

Referring to FIG. 4, the machine learning apparatus 300 may define a feature set including a plurality of features through the feature set definition unit 310 (step S410). The machine learning apparatus 300 may generate a plurality of feature combinations including n-dimensional features (where n is a natural number) for the feature set through the feature combination generation unit 320 (step S420).

In addition, the machine learning apparatus 300 may independently construct feature models for a plurality of feature combinations through the feature model analysis unit 330 (step S430), and may calculate prediction accuracy for the feature models as prediction results for a predetermined data set, respectively (step S440).

Also, the machine learning apparatus 300 may determine at least one good feature model that satisfies a preset criterion by aligning the feature models according to prediction accuracy through the good feature model determination unit 340 (step S450).

Thereafter, the machine learning apparatus 300 may extract only good genes that are frequently used in the good feature model as good features, and improve the performance of the model for use in electroencephalogram analysis step by step through the repetitive learning.

Figures 5, 6:
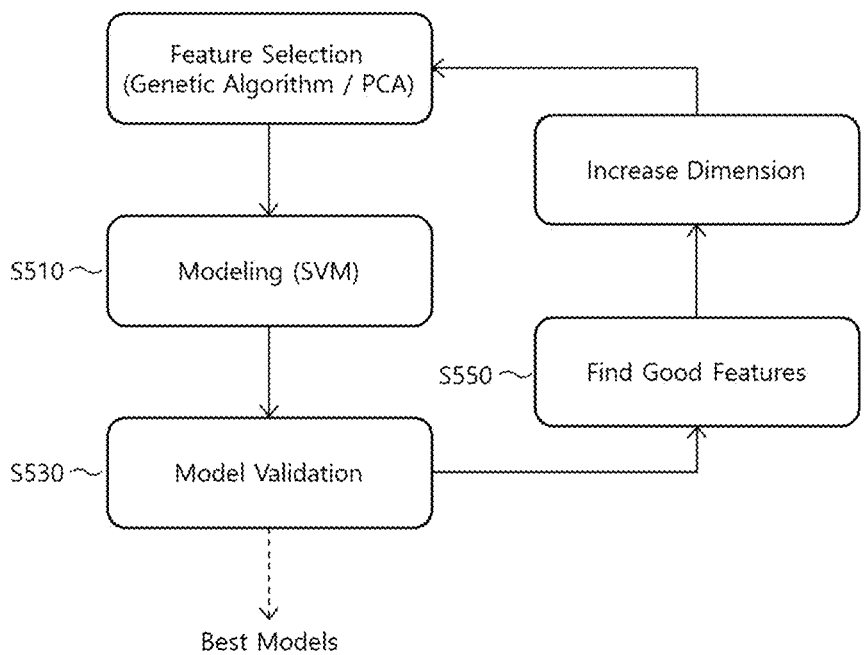
FIG. 5 is a diagram illustrating a steps feature selection process based on a genetic algorithm according to the present disclosure.
FIG. 6 is a diagram for describing an embodiment of a feature selection process according to the present disclosure.

FIG. 5 is a diagram illustrating a steps feature selection process based on a genetic algorithm according to the present disclosure.

Referring to FIG. 5, the machine learning apparatus 300 may construct independent features model for all possible feature combinations within a predetermined dimension (S510). When the feature model is constructed, the machine learning apparatus 300 may perform model verification (S530).

That is, the machine learning apparatus 300 may calculate the prediction accuracy for each model, determine the feature model having good performance in the prediction accuracy, and determine the good features (S550). Here, a good gene may correspond to a feature included in a model with high prediction performance, and as a high-dimensional model is constructed through repetitive operations, only the features corresponding to the good gene may survive.

In addition, the machine learning apparatus 300 may generate a higher-level feature model by including good genes, and may repeatedly perform the above process until the performance of the feature model no longer increases. As a result, the machine learning apparatus 300 selects good genes that have a great influence on the prediction result step by step and repeatedly performs learning and verification for prediction to finally generate the best performing feature models.

FIG. 6 is a diagram for describing an embodiment of a feature selection process according to the present disclosure.

Referring to FIG. 6, the machine learning method according to the present disclosure may be performed through a feature selection process defined by specific steps. More specifically, in Step1, a model can be created with all possible combinations within a predetermined dimension. In Step2, the accuracy of each model may be calculated and arranged in descending order based on the accuracy. In Step3, it is possible to separately collect a model (good feature model) 610 showing excellent performance above a certain standard. In Step4, it is possible to calculate which gene appears most frequently in the good feature model 610. In Step5, by setting a certain level, only good features 630 that are above the standard may be extracted. Finally, in Step6, a higher-level model can be generated by including the genes.

The machine learning method according to the present disclosure may proceed through a process in which steps 1 to 6 are repeatedly performed, and as a result of constructing a prediction model only with good features that affect predictive performance at each repetition, the final prediction model may have a high level of prediction accuracy.

FIG. 7 is a diagram for describing an embodiment of a feature set according to the present disclosure.

Referring to FIG. 7, the machine learning apparatus 300 according to the present disclosure may define and utilize a feature set for machine learning for electroencephalogram analysis. In FIG. 7, a row 710 may indicate a location in the 10/20 system, and a column 730 may indicate a frequency band of the electroencephalogram.

When only one feature is selected (hereinafter, one-dimensional modeling) through the combination of the electroencephalogram occurrence location and the electroencephalogram frequency band, the number of 19*8=152 cases can be derived (for example, Fp1*Delta). When performing machine learning modeling, 11,476 cases may be derived when two features are selected from among the features of FIG. 7 (hereinafter, two-dimensional modeling), and 573,800 cases may be derived when three features are selected.

Therefore, as the number of cases according to feature selection increases, it becomes difficult to handle the amount of computation. From four-dimensional modeling or more, a genetic algorithm can be applied to perform a modeling operation by combining only features that satisfy a specific criterion.

FIG. 8 is a diagram for describing a process of calculating the number of frequencies of features found in a good feature model according to the present disclosure.

Referring to FIG. 8, the machine learning apparatus 300 may determine a good feature model, and may determine a good feature based on the frequency number of features found in the good feature models.

For example, for 573,800 models generated in the three-dimensional modeling step, the machine learning apparatus 300 may verify whether the predicted value (Amyloid+/− or not) for each test set is equal to the actual value (Amyloid+/− or not). When it is assumed that the first feature model including [Fp1 delta, Fp2 delta, T3 theta] accurately predicts Amyloid+/− or not, and the second feature model including [Fp1 delta, Fp2 delta, F3 alpha1] predicts Amyloid+/− or not, the number of frequencies may be calculated for each feature.

Meanwhile, in the case of FIG. 8, the number of features found in models accurately predicting whether or not amyloid +/− may appear. Each feature may be aligned based on a frequency 810, and the machine learning apparatus 300 may determine the top k (k is a natural number) features as good features 830 according to the order of the frequency 810. In this case, the good features 830 are added as a feature set in the next step and may be used to determine a good feature model for a feature combination with an increased dimension.

Figures 11, 12:
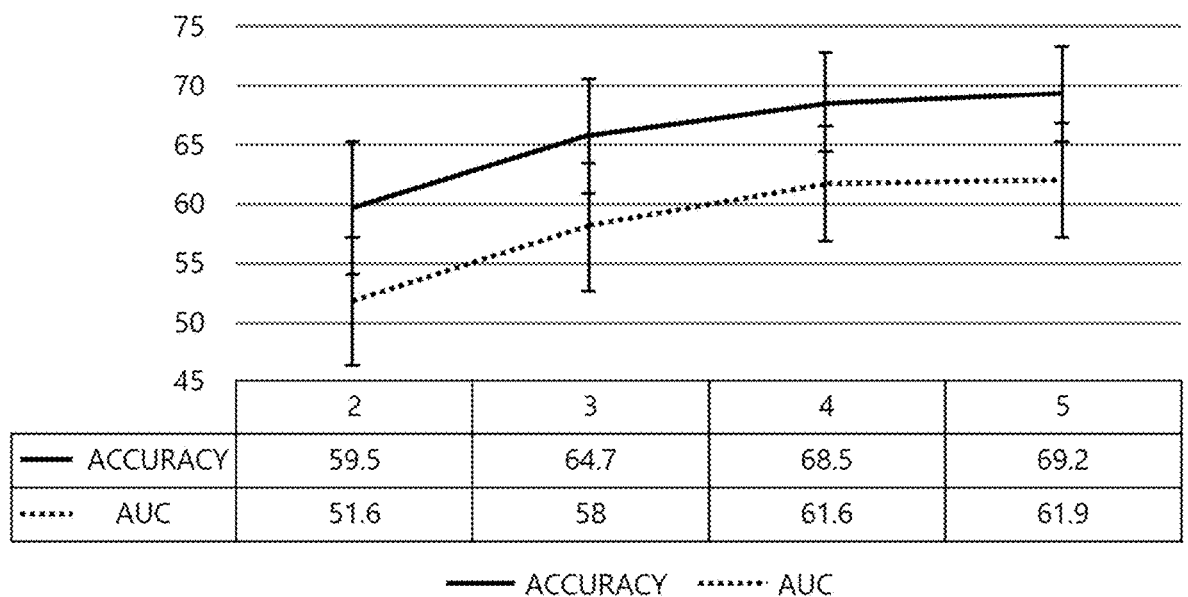

FIGS. 9 to 11 are diagrams for describing a reinforcement learning process for the good feature model according to the present disclosure.

Referring to FIGS. 9 to 11, the machine learning apparatus 300 may perform reinforcement learning on good prediction models. FIG. 9 may represent predicted values for test data of the best feature models of FIG. 5. In this case, the column may represent the best feature models, and the row may represent the predicted value of each of the best feature models for the test data. In addition, an average (score) 930 of predicted values of good feature models 910 for each test data is displayed on the right.

Here, the closer the average of the predicted value is to 21, the better it may correspond to predicting Normal Amyloid−. That is, in the case of a normal person, Amyloid—in which the amyloid protein does not normally exist in the brain may be common. Conversely, where there is mild cognitive impairment (MCI), Amyloid+, which causes the presence of amyloid protein in the brain, may appear.

Meanwhile, although 12 good feature models 910 are illustrated and described in FIG. 9, the present invention is not necessarily limited thereto, and may be operated using a variety of good feature models as needed.

FIG. 10 may correspond to the process of performing reinforcement learning for Amyloid −. Approaches to the reinforcement learning need to predict more accurately about the test data 1010 that the existing best feature models did not accurately predict, and may be based on the fact that the prediction is relatively accurate for the test data (the rest data), although the accuracy is somewhat lower, but the results are not affected.

More specifically, from above, test data1, 2, 3, . . . , 18, in the case of multiple of 1, the machine learning apparatus 300 may perform reinforcement learning by applying a reinforcement factor of 1.573 to test data 1 when accurately predicted, a reinforcement factor of 1.535 to test data 2 when accurately predicted, . . . , a reinforcement factor of 1.081 to test data 18 when accurately predicted. In this case, the reinforcement factor 1.573 of test data1 may be calculated through 1+0.573, and 0.573, a value (score) equal to or less than the decimal point, may be used in 21.573, which is the average (score) of the predicted value for test data1.

In addition, in the case of a multiple of 2, the machine learning apparatus 300 may perform reinforcement learning by applying a reinforcement factor of 2.146 to test data 1 when accurately predicted, a reinforcement factor of 2.07 to test data 2 when accurately predicted, . . . , a reinforcement factor of 1.162 to test data 18 when accurately predicted. In this case, the reinforcement factor 2.146 of test data1 may be calculated through 1+2*0.573, and +2, a value (score) equal to or less than the decimal point, may be used in 0.573, which is the average (score) of the predicted value for test data1.

On the other hand, it goes without saying that the above-mentioned multiples of 1 and 2 strengthening methods are merely examples and various methods may exist. For example, in the case of multiple of 2, the reinforcement factor of test data1 may be calculated through 1+2*0.508, and 0.508, the value after the decimal point, may be used from 21.508, which is the average (score) of the 1× predicted value for test data1.

FIG. 11 may correspond to a process performed for Amyloid+. More specifically, in the case of multiple of 1, the machine learning apparatus 300 may perform reinforcement learning by applying a reinforcement factor of 1.048 to test data 1 when accurately predicted, a reinforcement factor of 1.084 to test data 2 when accurately predicted, . . . , a reinforcement factor of 1.722 to test data 18 when accurately predicted. In this case, the reinforcement factor 1.048 of test data1 may be calculated through 1+(1−0.952), and 0.952, a value (score) equal to or less than the decimal point, may be used in −21.952, which is the average (score) of the predicted value for test data1. In addition, in the case of multiple of 2, the machine learning apparatus 300 may perform the same as the method of FIG. 10.

FIG. 12 is a diagram for describing a graph regarding performance of a machine learning model according to the present disclosure.

Referring to FIG. 12, the machine learning apparatus 300 may correspond to a graph representing machine learning performance for determining the presence or absence of amyloid that changes as the dimension of an actual genetic algorithm increases. That is, it may correspond to the average for the prediction accuracy and AUC of the best feature models of FIG. 5, and corresponds to the performance comparison result for 2 to 5 dimensional feature combinations (i.e., the number of features), respectively.

The machine learning method according to the present disclosure assumes that the power of each channel and each frequency band of the electroencephalogram is each gene, and may generate a model with all possible combinations within a given dimension. The machine learning method according to the present disclosure can calculate the performance of each model and collect models with excellent performance. The machine learning method according to the present disclosure may calculate which gene appears most frequently in a good model, and may be inferred that the more frequently a gene appears in a good model, the better the gene is needed to make a good model. The machine learning method according to the present disclosure may extract genes superior to the criterion by setting a certain level, and may generate a higher-level model using only the genes. The machine learning method according to the present disclosure may acquire a model close to the optimum as a result of repeatedly performing the above process.

Although exemplary embodiments of the present disclosure have been disclosed hereinabove, it may be understood by those skilled in the art that the present disclosure may be variously modified and altered without departing from the scope and spirit of the present disclosure described in the following claims.

DETAILED DESCRIPTION OF MAIN ELEMENTS

100: Electroencephalogram analysis system
300: Machine learning apparatus
610: Good feature module
630: Good feature
810: Frequency
830: Good feature
910: Good feature model
930: Average of predicted value

What is claimed is:

1. A machine learning method using steps feature selection based on a genetic algorithm, comprising:
defining a feature set including a plurality of features, wherein the defining of the feature set includes defining each of the plurality of features as a combination between an electroencephalogram occurrence location and an electroencephalogram frequency band for an electroencephalogram signal;
generating a plurality of feature combinations including n-dimensional features (n is a natural number) for the feature set;
independently constructing feature models for the plurality of feature combinations and calculating prediction accuracy for each of the feature models as a prediction result for a predetermined data set;
arranging the feature models according to the prediction accuracy to determine at least one feature model that satisfies a preset criterion;
determining a first feature from among features included in a corresponding feature set of the at least one feature model;
updating the feature set to include only the first feature and re-determining a feature model for a (n+1)-dimensional feature combination based on the updated feature set, and
diagnosing one or more pathological symptoms using the feature model for the (n+1)-dimensional feature combination,
wherein the calculating of each of the prediction accuracy includes calculating the prediction accuracy based on whether each of the feature models matches a predicted value and an actual value regarding the presence or absence of amyloid for the predetermined data set.

2. The machine learning method of claim 1, wherein the defining of the feature set includes determining a scalp electrode location depending on a 10-20 system as the electroencephalogram occurrence location, and separately determining the electroencephalogram frequency band into delta, theta, alpha, beta, and gamma according to a frequency component of the electroencephalogram signal.

3. The machine learning method of claim 1, wherein the generating of the plurality of feature combinations includes generating the plurality of feature combinations corresponding to all combinations including n features among the plurality of features.

4. The machine learning method of claim 1, wherein the determining of the feature model includes determining top m (m is a natural number) feature models as the at least one feature model according to the order of high prediction accuracy.

5. The machine learning method of claim 1, wherein the determining of the first feature includes counting the number of frequencies of each feature of the corresponding feature set and determining top k (k is a natural number) features as the first feature according to the order of high frequency.

6. The machine learning method of claim 1, wherein the re-determining of the feature model includes repeatedly performing a re-determining process on the feature model according to an update of the feature set and an increase in a dimension of the feature combination, and ending of the repetition of the re-determining process in a case where a difference between the prediction accuracy for the corresponding feature model and the prediction accuracy for the previous step is less than or equal to a preset reference value.

7. The machine learning method of claim 6, wherein the re-determining of the feature model includes comparing an average or minimum value of the corresponding prediction accuracy with the prediction accuracy for the previous step in a case where the number of corresponding feature models is plural.

8. The machine learning method of claim 1, further comprising:
performing reinforcement learning on the feature model according to the result of predicting the feature model for the predetermined data set.

9. The machine learning method of claim 8, wherein the performing of the reinforcement learning includes adjusting the corresponding predicted value by applying a reinforcement factor to the corresponding predicted value when the predicted result matches the actual value.

10. The machine learning method of claim 9, wherein the reinforcement factor is calculated by applying a specific multiple based on an average value of the predicted result when the number of feature models is plural.

11. The machine learning method of claim 10, wherein the reinforcement factor is calculated through the following equation based on the average value and the specific multiple.

$$\alpha = 1 + \beta * x \quad \text{[Equation]}$$

(where α denotes a reinforcement factor, β denotes a value less than or equal to a decimal point of the average value, and x denotes a specific multiple)

12. A machine learning system using steps feature selection based on a genetic algorithm, comprising:
a data processing apparatus; and
a memory device storing instructions that when executed by the data processing apparatus cause the server to perform operations comprising:
defining a feature set including a plurality of features, wherein the defining of the feature set includes defining each of the plurality of features as a combination between an electroencephalogram occurrence location and an electroencephalogram frequency band for an electroencephalogram signal;
generating a plurality of feature combinations including n-dimensional features (n is a natural number) for the feature set;
independently constructing feature models for the plurality of feature combinations and calculating prediction accuracy for each of the feature models as a prediction result for a predetermined data set;
aligning the feature models according to the prediction accuracy to determine at least one feature model that satisfies a preset criterion;
determining a first feature from among the features included in a corresponding feature set of the at least one feature model;
updating the feature set to include only the first feature and re-determining a feature model for a (n+1)-dimensional feature combination based on the updated feature set, and
diagnosing one or more pathological symptoms using the feature model for the (n+1)-dimensional feature combination.

13. The machine learning method of claim 1, wherein the first feature has a predetermined correlation with analysis information to be predicted through the at least one feature model.

14. The machine learning method of claim 13, wherein the predetermined correlation exceeds a predetermined value.

15. A non-transitory computer-readable medium having stored therein a program for causing a computer to execute a process of providing a machine learning method using steps feature selection based on a genetic algorithm, the process comprising:
defining a feature set including a plurality of features, wherein the defining of the feature set includes defining each of the plurality of features as a combination between an electroencephalogram occurrence location and an electroencephalogram frequency band for an electroencephalogram signal;
generating a plurality of feature combinations including n-dimensional features (n is a natural number) for the feature set;
independently constructing feature models for the plurality of feature combinations and calculating prediction accuracy for each of the feature models as a prediction result for a predetermined data set;
arranging the feature models according to the prediction accuracy to determine at least one feature model that satisfies a preset criterion;
determining a first feature from among features included in a corresponding feature set of the at least one feature model;
updating the feature set to include only the first feature and re-determining a feature model for a (n+1)-dimensional feature combination based on the updated feature set, and
diagnosing one or more pathological symptoms using the feature model for the (n+1)-dimensional feature combination,
wherein the calculating of each of the prediction accuracy includes calculating the prediction accuracy based on whether each of the feature models matches a predicted value and an actual value regarding the presence or absence of amyloid for the predetermined data set.

\* \* \* \* \*